(12) United States Patent
Takahashi

(10) Patent No.: US 10,289,907 B2
(45) Date of Patent: May 14, 2019

(54) IMAGE PROCESSING APPARATUS, IMAGE PICKUP APPARATUS, AND IMAGE PROCESSING METHOD

(71) Applicant: CANON KABUSHIKI KAISHA, Tokyo (JP)

(72) Inventor: Riuma Takahashi, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/632,954

(22) Filed: Jun. 26, 2017

(65) Prior Publication Data

US 2018/0012058 A1 Jan. 11, 2018

(30) Foreign Application Priority Data

Jul. 5, 2016 (JP) .................. 2016-133661

(51) Int. Cl.
| | |
|---|---|
| *A61B 3/10* | (2006.01) |
| *G06K 9/00* | (2006.01) |
| *G06T 7/00* | (2017.01) |
| *G06T 7/70* | (2017.01) |
| *G06T 11/60* | (2006.01) |
| *H04N 5/222* | (2006.01) |

(52) U.S. Cl.
CPC ............ *G06K 9/0057* (2013.01); *A61B 3/102* (2013.01); *G06T 7/97* (2017.01); *G06T 11/60* (2013.01); *G06T 7/70* (2017.01); *H04N 5/2226* (2013.01)

(58) Field of Classification Search
CPC ........... A61B 3/102; G06T 11/60; G06T 7/97; G06T 7/70; G06K 9/0057; H04N 5/2226
See application file for complete search history.

(56) References Cited

U.S. PATENT DOCUMENTS

| | | | | |
|---|---|---|---|---|
| 2010/0110376 A1* | 5/2010 | Everett | .................. | A61B 3/102 351/206 |
| 2011/0141259 A1* | 6/2011 | Nakano | ................ | A61B 3/0025 348/78 |
| 2014/0204341 A1* | 7/2014 | Murase | .................. | A61B 3/102 351/208 |
| 2015/0374227 A1* | 12/2015 | Takeno | .................. | A61B 3/102 600/425 |
| 2017/0065170 A1* | 3/2017 | Yamashita | ............. | A61B 3/102 |
| 2017/0227350 A1* | 8/2017 | Sarunic | ............. | G01B 9/02004 |

FOREIGN PATENT DOCUMENTS

| | | |
|---|---|---|
| JP | 2010220771 A | 10/2010 |
| JP | 2015093128 A | 5/2015 |

\* cited by examiner

*Primary Examiner* — Brenda C Bernardi
(74) *Attorney, Agent, or Firm* — Rossi, Kimms & McDowell LLP

(57) ABSTRACT

Provided is an image processing apparatus, including: an acquisition unit configured to acquire information on a layer boundary in tomographic structure of a current subject to be inspected; a determination unit configured to determine a depth range relating to a current en-face image of the subject to be inspected based on information indicating a depth range relating to a past en-face image of the subject to be inspected and the information on the layer boundary; and a generation unit configured to generate the current en-face image through use of data within the depth range relating to the current en-face image among pieces of three-dimensional data acquired for the current subject to be inspected.

30 Claims, 7 Drawing Sheets

IMAGE PROCESSING APPARATUS, IMAGE PICKUP APPARATUS, AND IMAGE PROCESSING METHOD

BACKGROUND

Field

The disclosure relates to an image processing apparatus, an image pickup apparatus, and an image processing method.

Description of the Related Art

Currently, an image pickup apparatus employing optical coherence tomography (hereinafter referred to as OCT) (the image pickup apparatus employing OCT is hereinafter referred to as "OCT apparatus") is being developed. In the OCT apparatus, light is radiated onto an object to cause interference between reflected light, which returns from different depths of the object depending on wavelengths of the radiated light, and reference light. Through analysis of frequency components included in a time waveform of the strength of the coherent light (hereinafter abbreviated as "interference spectrum"), the OCT apparatus can obtain information on a cross section of the object, and more specifically, a tomographic image. The OCT apparatus is used as an ophthalmologic image pickup apparatus in fundus inspection, for example.

When follow-up observation of a subject to be inspected using the OCT apparatus is performed, pieces of inspection data of the same part are acquired at different inspection dates and times, and a change in the same part of attention between the inspections is used for comparison. At this time, it is possible to save time and effort for operation by matching forms of display of tomographic images or the like between the inspections (see Japanese Patent Application Laid-Open No. 2010-220771). For example, when a tomographic image at a specific position of one piece of inspection data is displayed, follow-up observation can be performed efficiently by displaying a tomographic image at the same position also for a tomographic image of inspection data to be compared.

Meanwhile, in Japanese Patent Application Laid-Open No. 2015-93128, there is disclosed a method involving displaying, as an image that can be formed through use of OCT, based on three-dimensional data generated from a plurality of two-dimensional tomographic images, a two-dimensional image (en-face image) generated in a direction perpendicular to a cross-sectional plane of the two-dimensional tomographic images.

As used herein, the "en-face image" refers to a two-dimensional front image (en-face image) generated from data values of voxels within a desired depth range that is set to three-dimensional data (three-dimensional volume data) acquired by the OCT apparatus. In this case, the data value may be a pixel value of a three-dimensional image generated from the three-dimensional data. The data value may be, for example, a luminance value, or a value of a polarization parameter, for example, a retardation, which can be acquired through use of polarization. The data value may also be information on a cross section of the subject to be inspected, which is included in an interference spectrum of interference light. Examples of images that can be acquired through use of the technology for an en-face image include an en-face luminance image having a luminance value as its pixel value and an OCTA image acquired by angiography that uses OCT (OCT angiography: OCTA).

To generate the en-face image, it is necessary to specify a depth range in which the en-face image is generated from within the three-dimensional data. Further, when follow-up observation is performed through use of the en-face image, in all inspections to be compared, it is necessary to specify substantially the same regions corresponding to each other as a depth range in which the en-face image is generated, and thus the operation becomes complicated.

SUMMARY

The disclosure provides an image processing apparatus, an image pickup apparatus, and an image processing method, which are capable of generating an en-face image for efficiently performing follow-up observation of a subject to be inspected.

According to one embodiment of the disclosure, there is provided an image processing apparatus, including: an acquisition unit configured to acquire information on a layer boundary in tomographic structure of a current subject to be inspected; a determination unit configured to determine a depth range relating to a current en-face image of the subject to be inspected based on information indicating a depth range relating to a past en-face image of the subject to be inspected and the information on the layer boundary; and a generation unit configured to generate the current en-face image through use of data within the depth range relating to the current en-face image among pieces of three-dimensional data acquired for the current subject to be inspected.

According to another embodiment of the disclosure, there is provided an image pickup apparatus, including: an image pickup unit configured to image a subject to be inspected to acquire three-dimensional data including layer information on the subject to be inspected; a storage unit configured to store information indicating a depth range relating to a past en-face image of the subject to be inspected; a detection unit configured to detect, from pieces of three-dimensional data on a current subject to be inspected, a layer boundary in tomographic structure of the current subject to be inspected; a determination unit configured to determine, based on the information indicating the depth range relating to the past en-face image and the layer boundary, a depth range relating to a current en-face image of the subject to be inspected; and a generation unit configured to generate the current en-face image through use of data within the depth range relating to the current en-face image among the pieces of three-dimensional data on the current subject to be inspected.

According to still another embodiment of the disclosure, there is provided an image processing method, including: acquiring information on a layer boundary in tomographic structure of a current subject to be inspected; determining a depth range relating to a current en-face image of the subject to be inspected based on information indicating a depth range relating to a past en-face image of the subject to be inspected and the information on the layer boundary; and generating the current en-face image through use of data within the depth range relating to the current en-face image among pieces of three-dimensional data acquired for the current subject to be inspected.

Further features of the disclosure will become apparent from the following description of exemplary embodiments with reference to the attached drawings.

DESCRIPTION OF THE EMBODIMENTS

Figure 1:
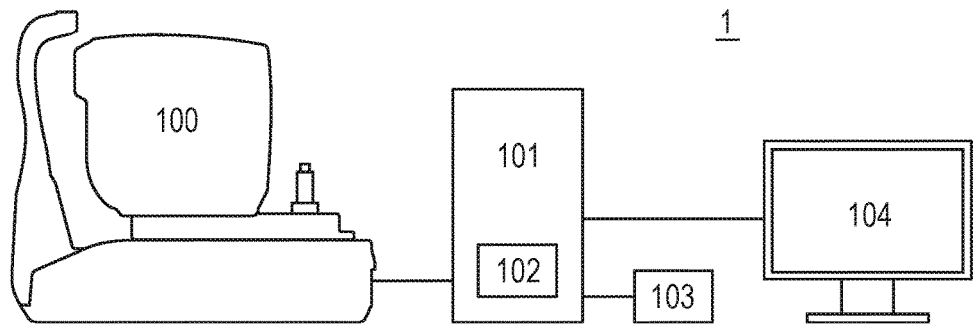
FIG. 1 is an illustration of an example of a schematic configuration of an image pickup apparatus according to a first embodiment.

Preferred embodiments of the disclosure will now be described in detail in accordance with the accompanying drawings. Note that, dimensions, materials, shapes, and relative positions of components, and others, which are described in the following embodiments, may be freely selected, and may be changed in accordance with a configuration of an apparatus to which the disclosure is applied or in accordance with various conditions. Further, in the drawings, the same reference symbols are used among the drawings to denote components that are identical or functionally similar to each other.

First Embodiment

Now, referring to FIG. 1 to FIG. 8, an OCT apparatus 1 is described as an image pickup apparatus according to a first embodiment of the disclosure. In the following description, it is assumed that a subject to be inspected is a human eye (eye to be inspected), but the subject to be inspected may be another organ or the like.

(Configuration of OCT Apparatus)

FIG. 1 is an illustration of an example of a schematic configuration of the OCT apparatus 1 according to the first embodiment. The OCT apparatus 1 includes an image pickup optical system 100, a signal processing apparatus 101, for example, a personal computer, a storage unit 102, an input unit 103, and a display unit 104, for example, a monitor.

The image pickup optical system 100 is an optical system for acquiring an image of an anterior ocular segment of the eye to be inspected, a scanning laser ophthalmoscope (SLO) fundus image of the eye to be inspected, and a tomographic image of a fundus of the eye to be inspected. The signal processing apparatus 101 is configured to, for example, control imaging performed by the image pickup optical system 100, analyze and generate an image (SLO image) picked up through use of SLO and a tomographic image of a fundus of the eye, and generate an en-face image. The signal processing apparatus 101 may be a computer dedicated to the OCT apparatus 1, or may be a general-purpose computer. The signal processing apparatus 101 may also be a computer integrated with the image pickup optical system 100. The storage unit 102 is configured to store a program for picking up a tomographic image, a program relating to an image processing method, patient information, imaged data, and statistical information of a normal database, and other such data. The storage unit 102 can be constructed of, for example, a hard disk drive or other such freely-selected storage device, or can be constructed of a RAM or a ROM. The input unit 103 is used to input an instruction to the signal processing apparatus 101. Specifically, the input unit 103 includes a keyboard and a mouse, for example.

(Configuration of Image Pickup Optical System)

Figure 2:
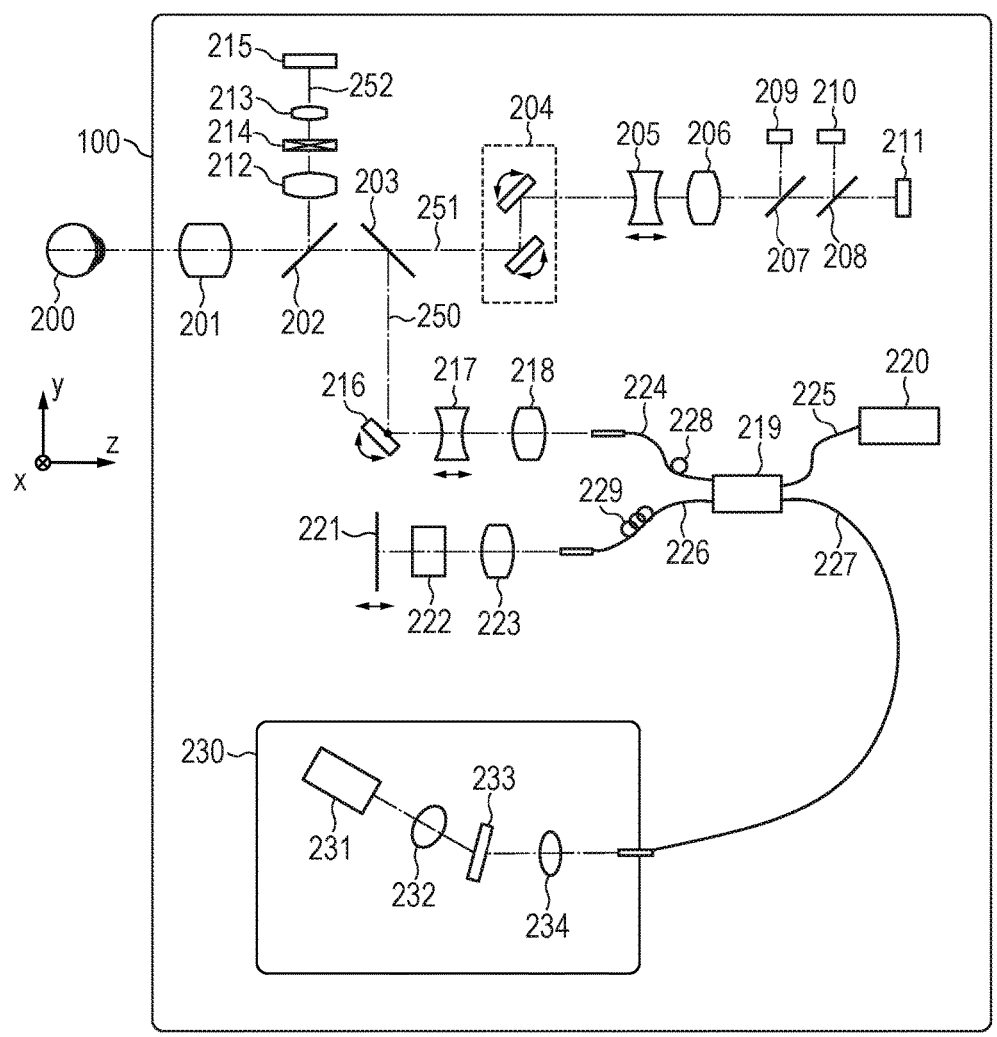
FIG. 2 is an illustration of an example of a schematic configuration of an image pickup optical system according to the first embodiment.

Referring to FIG. 2, a configuration of the image pickup optical system 100 is described. FIG. 2 is an illustration of an example of a schematic configuration of the image pickup optical system 100 (image pickup unit).

In the image pickup optical system 100, an objective lens 201 is arranged so as to be opposed to an eye to be inspected 200, and a first dichroic mirror 202 and a second dichroic mirror 203 are arranged on an optical axis of the objective lens 201. With those dichroic mirrors, an optical path from the eye to be inspected 200 is divided for each wavelength band into an optical path 250 for an OCT optical system, an optical path 251 for an SLO optical system and a fixation lamp, which is used for both of observation of the eye to be inspected 200 and acquisition of the SLO fundus image, and an optical path 252 for anterior ocular segment observation.

On the optical path 251 for the SLO optical system and the fixation lamp, there are arranged an SLO scanning unit 204, lenses 205 and 206, a mirror 207, a third dichroic mirror 208, a photodiode 209, an SLO light source 210, and a fixation lamp 211.

The SLO light source 210 is configured to emit light having a wavelength of approximately 780 nm as radiation light for SLO. The fixation lamp 211 is a light source for providing a fixation target for urging fixation of the eye to be inspected 200, and is configured to emit visible light corresponding to the fixation target.

The third dichroic mirror 208 is configured to reflect light from the SLO light source 210, and allow light from the fixation lamp 211 to pass therethrough, for each wavelength band. The third dichroic mirror 208 is arranged so as to allow those light beams to travel through the optical path 251 to enter the eye to be inspected 200. In the first embodiment, the third dichroic mirror 208 is configured to reflect the light from the SLO light source 210 and allow the light from the fixation lamp 211 to pass therethrough, but instead, the third dichroic mirror 208 may be configured to allow the light from the SLO light source 210 to pass therethrough and reflect the light from the fixation lamp 211.

The mirror 207 is a prism having a perforated mirror or a hollow mirror deposited thereon, and is configured to allow the radiation light emitted from the SLO light source 210 and the light emitted by the fixation lamp 211 to pass therethrough and reflect return light from the eye to be inspected 200, to thereby divide optical paths of those light beams. Instead, the mirror 207 may be configured to reflect the radiation light emitted from the SLO light source 210 and the light emitted by the fixation lamp 211 and allow the return light from the eye to be inspected 200 to pass therethrough.

The lens 205 is a lens for focusing of the SLO optical system and the fixation lamp (lens for focus adjustment). The lens 205 can be driven by a motor (not shown) along an optical axis of the light traveling through the optical path 251.

The SLO scanning unit 204 is configured to scan light emitted from the SLO light source 210 and the fixation lamp 211 on the eye to be inspected 200. The SLO scanning unit 204 includes an X scanner and a Y scanner, which are configured to scan those light beams in an x direction and a y direction on the eye to be inspected 200, respectively. In the first embodiment, the X scanner is constructed of a polygon mirror for performing high-speed scanning, and the Y scanner is constructed of a galvano mirror. The X scanner and the Y scanner can be constructed of any deflection mirrors that suit a desired configuration.

The photodiode 209 is configured to detect the return light from the eye to be inspected 200 of the radiation light emitted from the SLO light source 210. The photodiode 209 can generate, based on the detected light, an SLO signal for generating an SLO image of the eye to be inspected 200. The OCT apparatus 1 can transmit, with a control unit (not shown) or the like, the SLO signal to the signal processing apparatus 101 or an external server, for example. The signal processing apparatus 101 can generate, based on the SLO signal, an SLO image corresponding to a fundus image of the eye to be inspected 200.

Next, the light emitted from the SLO light source 210 and the light emitted from the fixation lamp 211 are described. The light emitted from the SLO light source 210 is reflected by the third dichroic mirror 208, passes through the mirror 207, travels through the lenses 206 and 205, and enters the SLO scanning unit 204. The light emitted from the SLO scanning unit 204 travels through the second dichroic mirror 203, the first dichroic mirror 202, and the objective lens 201, and enters the eye to be inspected 200. The SLO scanning unit 204 drives the X scanner and the Y scanner, to thereby scan the radiation light emitted from the SLO light source 210 on the eye to be inspected 200. The return light from the eye to be inspected 200 travels back through the same path as that of the radiation light, and is then reflected by the mirror 207 and guided to the photodiode 209. The photodiode 209 detects the return light from the eye to be inspected 200 that has entered photodiode 209 to generate the SLO signal. The OCT apparatus 1 can acquire the SLO fundus image from the SLO signal.

The light emitted from the fixation lamp 211 passes through the third dichroic mirror 208 and the mirror 207, travels through the lenses 206 and 205, and enters the SLO scanning unit 204. The light emitted from the SLO scanning unit 204 travels through the second dichroic mirror 203, the first dichroic mirror 202, and the objective lens 201, and enters the eye to be inspected 200. The SLO scanning unit 204 drives the X scanner and the Y scanner, to thereby scan the light emitted from the fixation lamp 211 on the eye to be inspected 200. At this time, by blinking the fixation lamp 211 in synchronization with the movement of the SLO scanning unit 204, it is possible to provide light having a freely-selected shape at a freely-selected position on the eye to be inspected 200 as the fixation target. In this manner, it is possible to urge fixation of a person to be inspected.

Next, the optical path 252 for anterior ocular segment observation is described. On the optical path 252 for anterior ocular segment observation, there are arranged lenses 212 and 213, a split prism 214, and a CCD 215 for anterior ocular segment observation, which is configured to detect infrared light.

On the optical path 252, light for anterior ocular segment observation having a wavelength of approximately 970 nm is emitted to the anterior ocular segment of the eye to be inspected 200 from a light source (not shown). Reflected light from the anterior ocular segment of the eye to be inspected 200 enters the split prism 214 via the objective lens 201, the first dichroic mirror 202, and the lens 212. The split prism 214 is arranged at a position conjugate with a pupil of the eye to be inspected 200. Light emitted from the split prism 214 enters the CCD 215 via the lens 213. The CCD 215 is configured to detect light having a wavelength of approximately 970 nm, and detect the reflected light from the anterior ocular segment to generate a signal corresponding to the reflected light from the anterior ocular segment. The OCT apparatus 1 can transmit, with the control unit (not shown), the signal from the CCD 215 to the signal processing apparatus 101 or the external server, for example. The signal processing apparatus 101 can generate, based on the signal generated by the CCD 215, an image of the anterior ocular segment of the eye to be inspected 200. At this time, the signal processing apparatus 101 can detect, from a split image of the anterior ocular segment, a distance from the image pickup optical system 100 to the eye to be inspected 200 in a Z direction (vertical direction) by detecting the reflected light that has passed through the split prism 214 with the CCD 215.

Next, the optical path 250 for the OCT optical system is described. The optical path 250 for the OCT optical system forms a part of the OCT optical system for picking up the tomographic image of the eye to be inspected 200. More specifically, the optical path 250 for the OCT optical system forms an optical path of measurement light for acquiring an interference signal to be used for generation of the tomographic image.

On the optical path 250 for the OCT optical system, there are arranged an XY scanner 216 and lenses 217 and 218. The XY scanner 216 is an OCT scanning unit for scanning light from the OCT light source 220 on the eye to be inspected 200. The XY scanner 216 illustrated as one mirror, but is actually constructed of two galvano mirrors configured to scan light in directions of two axes of an x axis and a y axis. The XY scanner 216 can be constructed through use of any deflection mirrors.

The lens 217 is a lens (for focus adjustment) for focusing the light from the OCT light source 220, which is emitted from an optical fiber 224 connected to an optical coupler 219, onto the eye to be inspected 200. The lens 217 can be driven by a motor (not shown) along an optical axis of the light traveling through the optical path 250. Through execution of the focusing through use of the lens 217, return light beams from the eye to be inspected 200 are simultaneously imaged into a spot shape onto a tip of the optical fiber 224 to enter the optical fiber 224.

Next, the optical path from the OCT light source 220 to the optical fiber 224, a reference optical system, and a configuration of a spectroscope 230, which are included in the OCT optical system, are described. In the OCT optical system, there are arranged the OCT light source 220, the optical coupler 219, single-mode optical fibers 224, 225, 226, and 227 connected to the optical coupler 219 to be integrated, a polarization adjustment unit 228, the reference optical system, and the spectroscope 230. In the reference optical system, there are arranged a reference mirror 221, a dispersion compensation glass 222, a lens 223, and a polarization adjustment unit 229. In the OCT optical system, those components and the respective optical components arranged on the optical path 250 form a Michelson interferometer.

The OCT light source 220 is a super luminescent diode (SLD), which is a representative low-coherent light source. The OCT light source 220 has a central wavelength of 855 nm and a wavelength bandwidth of approximately 100 nm. In this case, the bandwidth is an important parameter because the bandwidth affects a resolution in an optical axis direction of the tomographic image acquired through use of the OCT optical system.

While the SLD is selected as the OCT light source 220 in the first embodiment, another type of light source may be used as the OCT light source 220. The OCT light source 220 only needs to emit low-coherent light, and for example, an amplified spontaneous emission (ASE) light source may be used as the OCT light source 220. The central wavelength of the OCT light source 220 can be set to that of near-infrared light in view of the configuration in which the subject to be inspected is an eye. Further, the central wavelength affects a lateral resolution of the acquired tomographic image, and hence a light source whose central wavelength is as short as possible can be used. In the first embodiment, because of both reasons, the light source having the central wavelength of 855 nm is used as the OCT light source 220.

The light emitted from the OCT light source 220 travels through the optical fiber 225 and enters the optical coupler 219. The optical coupler 219 divides the light that has entered the optical coupler 219 into the measurement light to travel toward the optical fiber 224 and reference light to travel toward the optical fiber 226.

The measurement light travels through the polarization adjustment unit 228 and the optical fiber 224 to enter the optical path 250. The polarization adjustment unit 228 is configured to adjust a polarization state of the measurement light. The measurement light travels through the optical path 250, and is radiated onto the eye to be inspected 200 being an imaging target. The measurement light is reflected or scattered by the eye to be inspected 200, and travels through the same optical path as the return light to reach the optical coupler 219.

Meanwhile, the reference light travels through the polarization adjustment unit 229, the optical fiber 226, the lens 223, and the dispersion compensation glass 222, which is inserted in order to match dispersions of the measurement light and the reference light, and reaches the reference mirror 221 to be reflected by the reference mirror 221. The polarization adjustment unit 229 is configured to adjust a polarization state of the reference light. The reference light reflected by the reference mirror 221 travels through the same optical path as the return light to reach the optical coupler 219.

In this case, the polarization adjustment unit 228 is a polarization adjustment unit on the measurement light side, which is arranged on the optical fiber 224, and the polarization adjustment unit 229 is a polarization adjustment unit on the reference light side, which is arranged on the optical fiber 226. Those polarization adjustment units 228 and 229 include several looped portions formed by pulling around the respective optical fibers. The polarization adjustment units 228 and 229 rotate the looped portions about longitudinal directions of the optical fibers to apply torsion to the fibers, and can thus adjust the polarization states of the light traveling through the optical fibers. Accordingly, through use of the polarization adjustment units 228 and 229, the respective polarization states of the measurement light and the reference light can be adjusted to be matched.

The return light of the measurement light and the return light of the reference light that have reached the optical coupler 219 are coupled by the optical coupler 219 to become interference light. Interference occurs in the measurement light and the reference light when an optical path length of the measurement light and an optical path length of the reference light become approximately the same. In this case, the reference mirror 221 is held so as to be capable of being adjusted in the optical axis direction by a motor and a drive mechanism (both not shown), and through movement of the reference mirror 221 in the optical axis direction, the optical path length of the measurement light, which varies depending on the eye to be inspected 200, can be matched with the optical path length of the reference light. The interference light generated in the optical coupler 219 is guided to the spectroscope 230 via the optical fiber 227.

In the spectroscope 230, there are arranged lenses 232 and 234, a diffraction grating 233, and a line sensor 231. The interference light emitted from the optical fiber 227 passes through the lens 234 to become collimated light, and is then dispersed by the diffraction grating 233 and imaged onto the line sensor 231 by the lens 232. The line sensor 231 configured to detect the imaged interference light to generate an OCT interference signal containing layer information on the eye to be inspected 200. The image pickup optical system 100 can transmit, with the control unit (not shown), the OCT interference signal to the signal processing apparatus 101 or the external server, for example. The signal processing apparatus 101 can generate the tomographic image of the eye to be inspected 200 based on the OCT interference signal.

With the configuration described above, the OCT apparatus 1 can acquire the tomographic image of the eye to be inspected 200 and acquire a high-contrast SLO fundus image of the eye to be inspected 200 even with near-infrared light.

(Structure of Imaged Data and En-Face Image)

Figure 3:
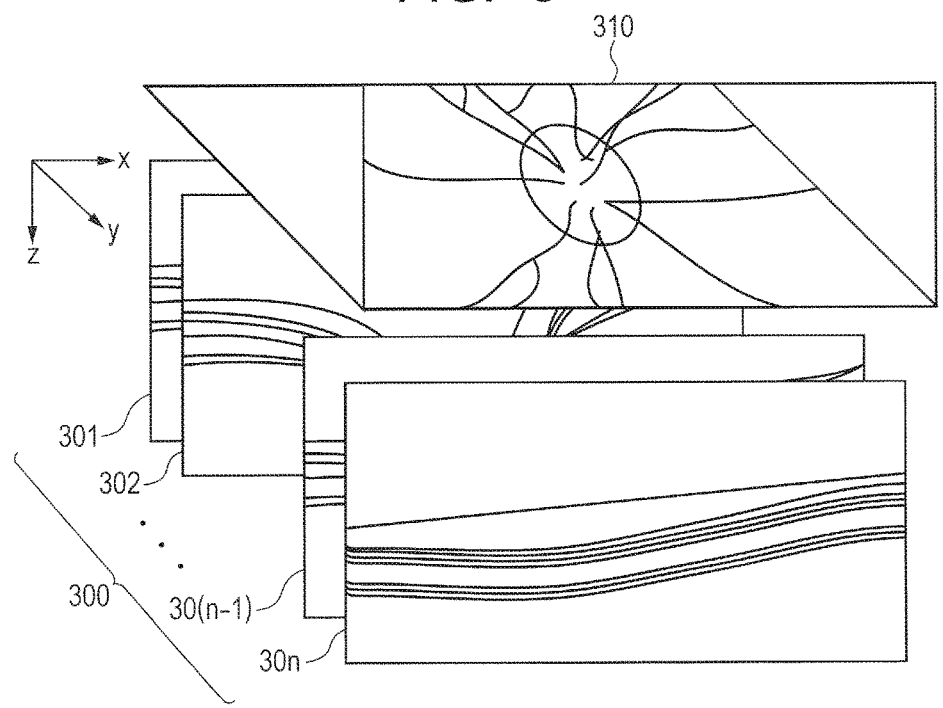
FIG. 3 is a diagram for illustrating structure of data on acquired tomographic images of a subject to be inspected.

Referring to FIG. 3, the structure of three-dimensional data on cross sections of the eye to be inspected 200 that are acquired by the image pickup optical system 100 and the structure of the en-face image are described. FIG. 3 is a diagram for illustrating the structure of the data acquired by the image pickup optical system 100.

The OCT apparatus 1 can acquire the tomographic image 301 by imaging the eye to be inspected 200 with the image pickup optical system 100 and reconfiguring data on the acquired OCT interference signal with the signal processing apparatus 101. The OCT apparatus 1 images the eye to be inspected 200 successively in a y-axis direction with the acquired tomographic image 301 being set as an x-z axis plane. In this manner, the OCT apparatus 1 can acquire three-dimensional data 300 formed by tomographic images 301 to 30n on a specific region of the fundus of the eye to be inspected 200. The number n may be set to any number that suits a desired configuration. Further, while the three-dimensional data 300 is data formed by the tomographic images 301 to 30n in this case, the three-dimensional data may be data formed by two-dimensional data (OCT interference signal) corresponding to the tomographic images 301 to 30n.

Further, the en-face image 310 can be generated by generating, with the signal processing apparatus 101, an image on an x-y axis plane from the acquired three-dimensional data 300. More specifically, the signal processing apparatus 101 uses, at each pixel position in y axis directions, data within a predetermined range (depth range) in a depth direction of the three-dimensional data 300 to determine a pixel value of the pixel position, to thereby acquire the en-face image 310. In the signal processing apparatus 101 according to the first embodiment, at each pixel position in the x-y axis directions, a value obtained by integrating pieces of data (pixel values) within the predetermined range in the depth direction of the three-dimensional data 300 is determined as the pixel value of the pixel position, to thereby generate the en-face image 310.

When the en-face image 310 is generated from the three-dimensional data 300, instead of integrating the pieces of data within the predetermined range in the depth direction, the pieces of data may be added and averaged for each pixel position to determine the pixel value of the pixel position. As another example, a representative value may be determined for each pixel position from the pieces of data within the predetermined range in the depth direction, and the representative value may be determined as the pixel value of the pixel position. As a method of determining the representative value, the pieces of data within the predetermined range in the depth direction may be sorted in ascending or descending order of values of the pieces of data, and a median value of the values may be determined as the representative value. As another example, the largest value, the smallest value, or an average value of the pieces of data within the predetermined range in the depth direction may be determined as the representative value.

(Configuration of Image Processing Apparatus)

Figure 4:
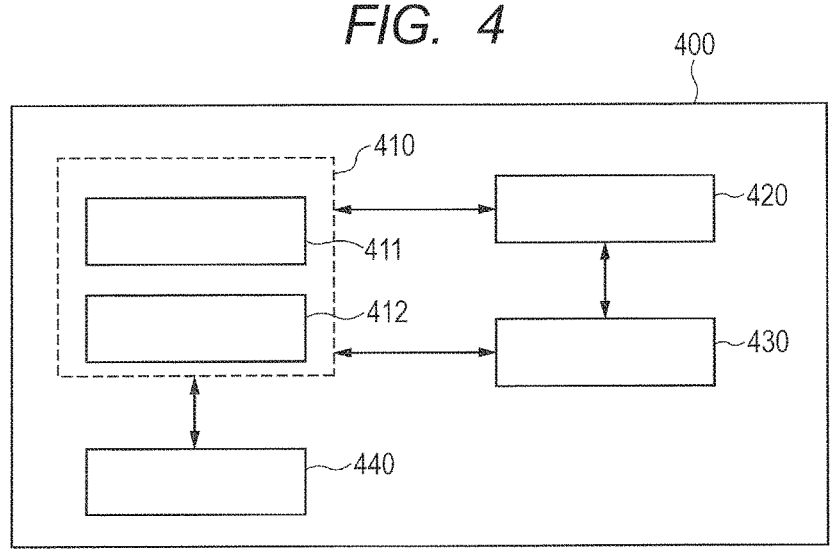
FIG. 4 is a block diagram for illustrating an example of a schematic configuration of an image processing apparatus according to the first embodiment.

Referring to FIG. 4, an image processing apparatus 400 according to the first embodiment is described. FIG. 4 is a block diagram for illustrating an example of a schematic configuration of the image processing apparatus 400 according to the first embodiment.

The image processing apparatus 400 includes an image processing unit 410, a storage unit 420, a determination unit 430, and a display unit 440. The image processing unit 410 includes a generation unit 411 and a detection unit 412 (acquisition unit). The image processing unit 410 and the determination unit 430 correspond to the signal processing apparatus 101 of FIG. 1, the storage unit 420 corresponds to the storage unit 102 of FIG. 1, and the display unit 440 corresponds to the display unit 104 of FIG. 1.

The detection unit 412 is configured to detect a boundary between layers (layer boundary) of tomographic structure for each piece of two-dimensional data (tomographic images 300 to 30n) included in the three-dimensional data 300 on the eye to be inspected 200 newly acquired by the image pickup optical system 100. Specifically, the detection unit 412 detects, at each x-y position of the three-dimensional data 300, a portion where a difference in contrast between pieces of data in the depth direction (z axis direction) is larger than a predetermined threshold as the layer boundary. Further, the detection unit 412 can refer to a template regarding the tomographic structure (including the names of layers and others) stored in the storage unit 420 or the like to identify each layer the tomographic image based on the detected layer boundary. The data for acquiring the difference in contrast may be luminance values in the tomographic images 301 to 30n, or may be data of the OCT interference signal.

The storage unit 420 configured to store information on the depth range of the three-dimensional data, which was used to generate the en-face image for the eye to be inspected 200 in the past. Thus, the image processing apparatus 400 can retrieve from the storage unit 420 the information on the depth range relating to the past en-face image of the eye to be inspected 200. The storage unit 420 can also store, for example, information on the past en-face image of the eye to be inspected 200, an inspection date and time, and the person to be inspected, and a template regarding the tomographic structure.

The determination unit 430 is configured to determine, based on the information on the layer boundary acquired from the detection unit 412 and the information on the depth range relating to the past en-face image retrieved from the storage unit 420, the depth range for generating the en-face image 310 of the three-dimensional data 300 that is newly acquired. The generation unit 411 is configured to generate a current en-face image 310 of the eye to be inspected 200 through use of use data within the depth range determined by the determination unit 430 among the pieces of three-dimensional data 300. The display unit 440 is configured to display the en-face image 310 generated by the generation unit 411.

(Configuration of Display Screen)

Figure 5:
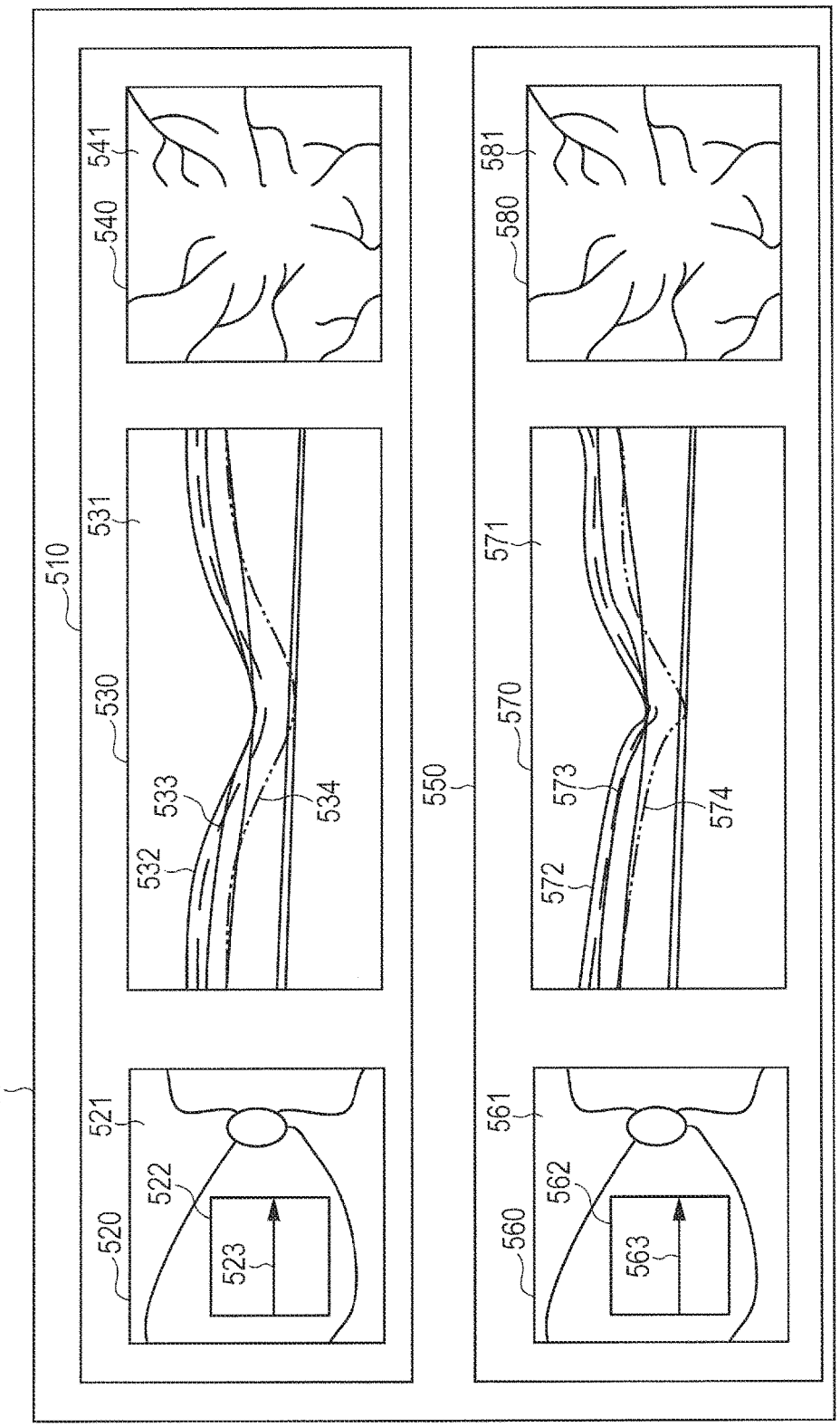
FIG. 5 is an illustration of an example of a screen to be displayed on a display unit.

Referring to FIG. 5, a configuration of a display screen of the first embodiment is described. FIG. 5 is an illustration of an example of a screen to be displayed on the display unit 440 of the first embodiment.

A display screen 500 includes a current data display area 510 for displaying the imaged data acquired by the image pickup optical system 100 from the current eye to be inspected 200, and a past data display area 550 for displaying the past imaged data of the eye to be inspected 200 acquired from the storage unit 420. The current data display area 510 includes a fundus display area 520 for displaying a fundus image, a layer display area 530 for displaying a tomographic image, an en-face display area 540 for displaying an en-face image. Further, the past data display area 550 includes a fundus display area 560, a layer display area 570, and an en-face display area 580.

In the fundus display areas 520 and 560, fundus images 521 and 561, three-dimensional data ranges 522 and 562, tomographic image position indicators 523 and 563 are displayed, respectively. As the fundus images 521 and 561, SLO images that can be acquired from the image pickup optical system 100 are displayed. The fundus images 521 and 561 only need to be fundus images within a range that is wider than or equivalent to that of the three-dimensional data in the x-y axis plane. The fundus images 521 and 561 may be images acquired for the same eye to be inspected 200 by a fundus image pickup apparatus other than the image pickup optical system 100, or may be images obtained by reconfiguring fundus images from the three-dimensional image acquired by the image pickup optical system 100.

The three-dimensional data ranges 522 and 562 indicate ranges in which the eye to be inspected 200 is imaged to acquire the three-dimensional data. Through display of the three-dimensional data ranges 522 and 562 on the fundus images 521 and 561, respectively, it is possible to indicate a positional relationship of a range in which the three-dimensional data is acquired with respect to the fundus of the eye to be inspected 200. Positional information on the three-dimensional data ranges 522 and 562 can be registered in a database, for example, the storage unit 420 together with the three-dimensional data simultaneously with the imaging performed by the image pickup optical system 100.

The tomographic image position indicators 523 and 563 are indicators indicating positions where tomographic images 531 and 571 displayed in the layer display areas 530 and 570 are picked up, respectively. The arrows of the tomographic image position indicators 523 and 563 indicate main-scanning directions of the measurement light at the time of acquisition of the tomographic images 531 and 571, respectively.

In the layer display areas 530 and 570, the tomographic images 531 and 571, layer boundaries 532 and 572, en-face generation range upper ends 533 and 573, and en-face generation range lower ends 534 and 574 are displayed, respectively. In FIG. 5, in order to distinguish those two types of ends, the en-face generation range upper ends 533 and 573 are indicated by the broken lines, and the en-face generation range lower ends 534 and 574 are indicated by the two-dot chain lines. The lines indicating those two types of ends may be any types of lines.

The tomographic images 531 and 571 are tomographic images of the eye to be inspected 200 at the positions of (corresponding to) the tomographic image position indicators 523 and 563 of the fundus display areas 520 and 560, respectively. The positions of the tomographic image position indicators 523 and 563 may be changed based on operator's input or the like, and in response to changes in the positions of the tomographic image position indicators 523 and 563, the tomographic images corresponding to the tomographic images 531 and 571 also change, respectively.

The layer boundaries 532 and 572 are each an example of a line indicating each layer boundary detected by the detection unit 412. The en-face generation range upper ends 533 and 573 and the en-face generation range lower ends 534 and 574 are lines indicating the depth ranges (generation ranges) used when en-face images 541 and 581 to be displayed the en-face display areas 540 and 580 are generated, respectively.

In the en-face display areas 540 and 580, the en-face images 541 and 581 are displayed, respectively. The en-face image 541 is an en-face image generated by the generation unit 411 from data within the depth range between the en-face generation range upper end 533 and the en-face generation range lower end 534 of the tomographic image 531. Further, the en-face image 581 is an en-face image generated by the generation unit 411 from data within the depth range between the en-face generation range upper end 573 and the en-face generation range lower end 574 of the tomographic image 571.

While the display screen 500 is configured as described above in the first embodiment, the display screen 500 only needs to be configured such that the current en-face image 541 is generated based on the information on the depth range relating to the past en-face image as described later and the generated en-face image 541 is displayed on the en-face display area 540. Further, while an example of imaged data of the fundus of the eye is displayed on the display screen 500 in the first embodiment, imaged data of a part other than the fundus of the eye, for example, an anterior ocular segment may also be displayed on the display screen 500.

(Flow of Image Processing)

Figure 6:
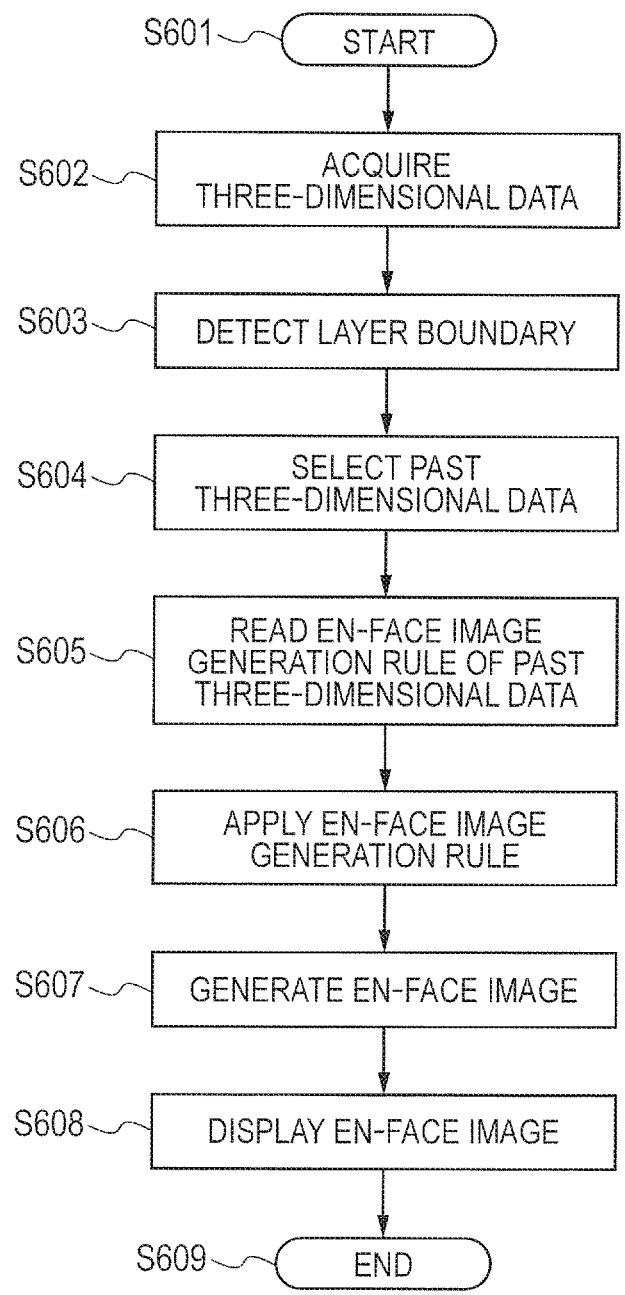
FIG. 6 is a flowchart for illustrating processing to be performed by the image processing apparatus according to the first embodiment.

Referring to FIG. 6, a flow of processing an en-face image by the image processing apparatus 400 is described. FIG. 6 is a flowchart for illustrating processing to be performed by the image processing apparatus 400.

When image processing is started in Step S601, in Step S602, the image processing unit 410 of the image processing apparatus 400 acquires the three-dimensional data 300 on the current eye to be inspected 200. Specifically, imaging is performed by the image pickup optical system 100 to acquire the three-dimensional data 300.

Next, in Step S603, the detection unit 412 of the image processing apparatus 400 analyzes the acquired three-dimensional data 300 to detect a boundary line (layer boundary) of each layer of the tomographic structure of the current eye to be inspected 200. In the first embodiment, to detect the layer boundary, as described above, in the layer information included in the three-dimensional data 300, a portion where a difference in contrast between pieces of data in the depth direction is detected as the layer boundary. The method of detecting the layer boundary is not limited thereto, and the layer boundary may be detected by any method. Further, the image processing unit 410 can refer to the template stored in the storage unit 420 or the like for the detected layer boundary to identify and determine each layer boundary and layers sandwiched between the layer boundaries. As the layer boundary to be determined, there are given, for example, ILM (retina-vitreous body boundary), an NFL/GCL boundary, a GCL/IPL boundary, an IPL/INL boundary, an IS/OS line, RPE, and BM.

Next, in Step S604, the image processing unit 410 selects from the storage unit 420 the three-dimensional data (past inspection data) on the past eye to be inspected 200 to be compared in follow-up observation. In the first embodiment, the image processing unit 410 automatically selects data that is older than the current three-dimensional data 300 and is the latest among pieces of past three-dimensional data acquired for the same patient, the same left or right eye, and the same part. The past three-dimensional data can be automatically selected as follows: when the three-dimensional data is acquired by the image pickup optical system 100, information on a date and the person to be inspected is also acquired and stored in the storage unit 420, and those pieces of information and pieces of information on the current three-dimensional data 300 are compared with each other. As other examples, the past three-dimensional data to be compared may be selected by manually selecting the data by the operator, or retrieving from data stored in the storage unit 420 past three-dimensional data (including data on other persons) that is close to the condition of the subject in terms of a layer boundary shape or a case, and selecting the retrieved data.

Next, in Step S605, for the past three-dimensional data selected in Step S604, the determination unit 430 acquires from the storage unit 420 an en-face image generation rule used when the en-face image (past en-face image) was generated. As used herein, the "en-face image generation rule" refers to information on the depth range of the three-dimensional data, which is used when the en-face image is generated. More specifically, the en-face image generation rule is information defining positions of the en-face generation range upper end 533 or 573 and the en-face generation range lower end 534 or 574, which define the depth range in the three-dimensional data from which the en-face image is generated. The en-face image generation rule can include, for example, a specific layer boundary, an offset amount from a specific layer boundary, or an internal ratio within a specific layer.

Figure 7:
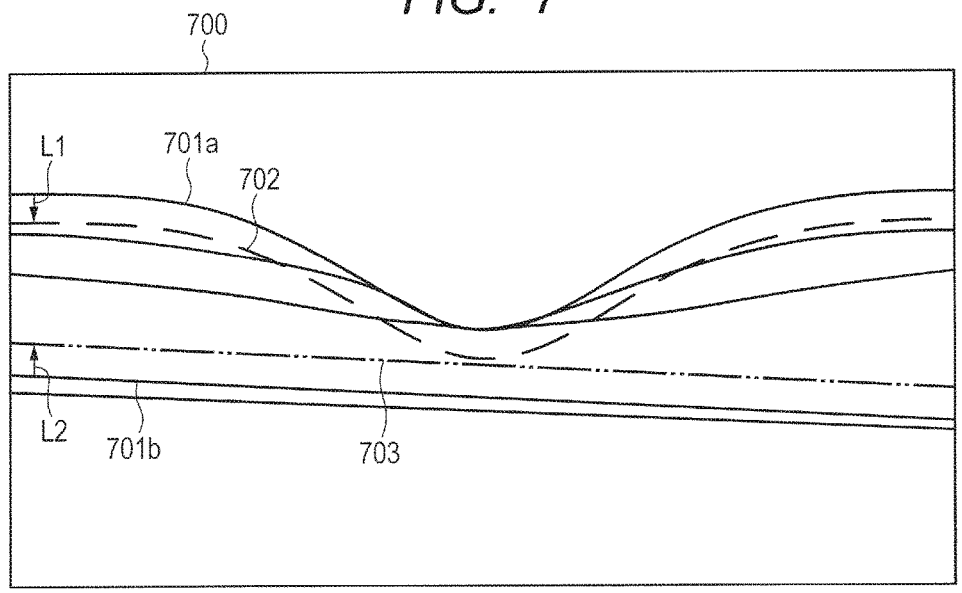
FIG. 7 is an illustration of an example of a case where a distance from a freely-selected layer boundary is set as an en-face image generation rule.
Figure 8:
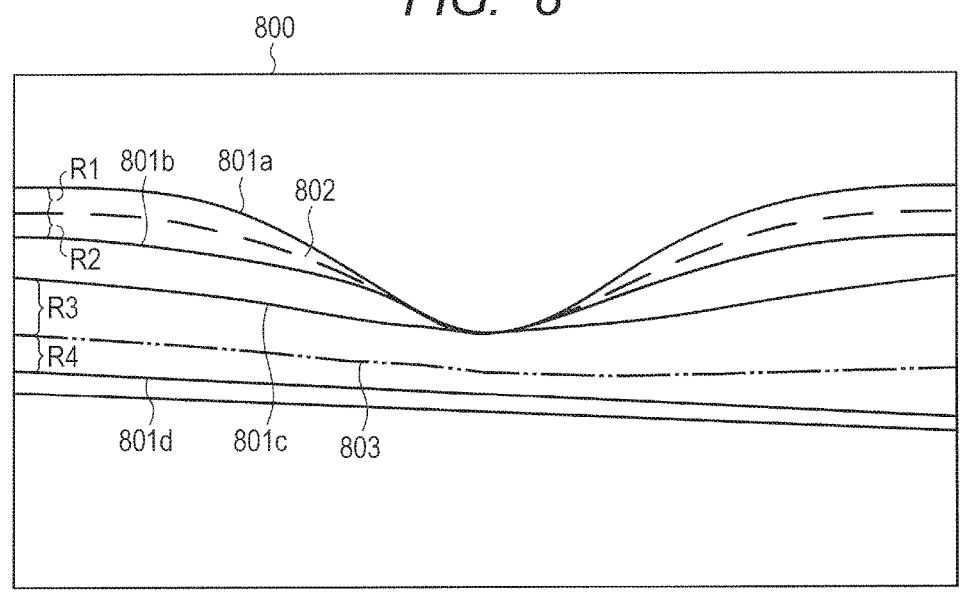
FIG. 8 is an illustration of an example of a case where an internal ratio between freely-selected layers is set as the en-face image generation rule.

Referring to FIG. 7 and FIG. 8, a specific en-face image generation rule is described. FIG. 7 is an illustration of an example of a case where a distance from a specific layer boundary is set as the en-face image generation rule. In FIG. 7, in order to distinguish the two types of ends, an en-face generation range upper end 702 is indicated by the broken line, and an en-face generation range lower end 703 is indicated by the two-dot chain lines. The lines indicating those two types of ends may be any types of lines. Further, in FIG. 7 and FIG. 8, an upper side and a lower side correspond to an upper side and a lower side in the tomographic image, respectively, and a shallower direction and a deeper direction in the depth direction are defined as an upper direction and a lower direction, respectively.

In a tomographic image 700, layer boundaries 701a and 701b, the en-face generation range upper end 702, and the en-face generation range lower end 703 are shown. In this example, the en-face generation range upper end 702 is separated from the layer boundary 701a, which is the uppermost layer boundary, by a distance L1 in the lower direction. Further, the en-face generation range lower end 703 is separated from the layer boundary 701b, which is the second lowermost layer boundary, by a distance L2 in the upper direction.

The storage unit 420 stores, as the en-face image generation rule, the layer boundaries 701a and 701b and the distances L1 and L2, which correspond to positional information on the en-face generation range upper end 702 and the en-face generation range lower end 703 that were set the past three-dimensional data. In Step S605, the determination unit 430 acquires the en-face image generation rule from the storage unit 420, and in Step S606, applies the acquired en-face image generation rule to the current three-dimensional data 300.

At this time, the determination unit 430 determines the depth range for the current en-face image 310 based on the acquired en-face image generation rule and the layer boundaries in the current three-dimensional data 300 on the eye to be inspected 200. More specifically, the determination unit 430 sets, based on the acquired en-face image generation rule, an en-face generation range upper end at a position separated by the distance L1 in the lower direction from the uppermost layer boundary in the current three-dimensional data 300 on the eye to be inspected 200. Further, the determination unit 430 sets, based on the acquired en-face image generation rule, an en-face generation range lower end at a position separated by the distance L2 in the upper direction from the second lowermost layer boundary in the current three-dimensional data 300 on the eye to be inspected 200.

With this configuration, the image processing apparatus 400 can accurately generate an en-face image within a range (depth range) between positions separated by predetermined distances from predetermined layer boundaries, and can thus enhance accuracy of comparison at the time of follow-up observation of the eye to be inspected 200. Specific layer boundaries in the en-face image generation rule are not limited to the above-mentioned uppermost layer boundary and second lowermost layer boundary, and may be any layer boundaries. Further, the distances L1 and L2 may also be set freely.

FIG. 8 is an illustration of an example of a case where a ratio between distances from specific two layer boundaries (internal ratio) is set as the en-face image generation rule. In FIG. 8, in order to distinguish the two types of ends, an en-face generation range upper end 802 is indicated by the broken line, and an en-face generation range lower end 803 is indicated by the two-dot chain line. The lines indicating those two types of ends may be any types of lines.

In a tomographic image 800, layer boundaries 801a, 801b, 801c, and 801d, the en-face generation range upper end 802, and the en-face generation range lower end 803 are shown. In this example, the en-face generation range upper end 802 is set at a position where a layer between the layer boundary 801a and the layer boundary 801b is internally divided at a ratio of R1:R2. Further, the en-face generation range lower end 803 is set at a position where a layer between the layer boundary 801c and the layer boundary 801d internally divided at a ratio of R3:R4.

In this example, the storage unit 420 stores the ratio between the distances from specific two layer boundaries as the en-face image generation rule. Specifically, the storage unit 420 stores the layer boundaries 801a, 801b, 801c, and 801d and the ratios R1:R2 and R3:R4 as the en-face image generation rule. Instead of the ratios, the storage unit 420 may simply store the values R1, R2, R3, and R4 of the ratios. As in the case of storing the distances L1 and L2 in the example illustrated in FIG. 7, in Step S605, the determination unit 430 acquires the en-face image generation rule from the storage unit 420, and in Step S606, applies the en-face image generation rule to the current three-dimensional data 300.

At this time, the determination unit 430 determines the en-face generation range upper end and the en-face generation range lower end based on the acquired en-face image generation rule and the layer boundary in the current three-dimensional data 300 on the eye to be inspected 200. More specifically, the determination unit 430 sets, based on the acquired en-face image generation rule, the en-face generation range upper end at a position where a layer between layer boundaries corresponding to the layer boundaries 801a and 801b in the current three-dimensional data 300 on the eye to be inspected 200 is internally divided at the ratio of R1:R2. Further, the determination unit 430 sets, based on the acquired en-face image generation rule, the en-face generation range lower end at a position where a layer between layer boundaries corresponding to the layer boundaries 801c and 801d in the current three-dimensional data 300 on the eye to be inspected 200 is internally divided at the ratio of R3:R4.

With this configuration, the image processing apparatus 400 can accurately generate an en-face image within a range (depth range) between positions in predetermined layers where the predetermined layers are internally divided at predetermined ratios. For example, when the thickness of a layer is found in the follow-up observation to be greatly changed due to an edema or the like, in the example illustrated in FIG. 7 in which the en-face generation range is determined through use of the distances, data to be used for generation of the en-face image may fall outside the en-face generation range. In contrast, in the above-mentioned example, the en-face generation range is determined through use of the internal ratios within the layer boundaries, and hence even when the thickness of a layer is greatly changed, data to be used for generation of the en-face image can be prevented from falling outside the en-face generation range. A specific layer boundary and the internal ratio in the en-face image generation rule may be freely set.

While the two patterns of en-face image generation rules are given in the above description, the en-face image generation rule is not limited thereto. The en-face image generation rule may be another rule, for example, a rule simply including two layer boundaries as the en-face generation range. Further, the image processing unit 410 may also be configured to allow a user to easily switch the en-face image generation rule among the above-mentioned two patterns and other patterns of en-face image generation rules.

In Step S606, the determination unit 430 applies the en-face image generation rule read in Step S605 to the three-dimensional data 300 on the current eye to be inspected 200 so that the generation unit 411 may generate the en-face image 310 of the current three-dimensional data 300. At this time, the determination unit 430 applies information on a specific layer boundary included in the en-face image generation rule, for example, the above-mentioned layer boundaries 701a and 701b, to information on the layer boundary of the current eye to be inspected 200 determined in Step S603. The determination unit 430 applies the en-face image generation rule to the current three-dimensional data 300, to thereby determine the en-face generation range for the current three-dimensional data 300.

Next, in Step S607, the generation unit 411 generates the current en-face image 310 of the eye to be inspected 200 through use of data within the en-face generation range determined by the determination unit 430 among pieces of the current three-dimensional data 300. In the first embodiment, the generation unit 411 uses the following expression to calculate each pixel value of the current en-face image 310. In the expression, EnFace(x,y) represents a pixel value of the en-face image 310 at coordinates (x,y). Further, Dhigh(x,y) and Dlow(x,y) represent positions of upper and lower ends of a range in which the en-face image 310 is generated, respectively, and Img(x,y,z) represents data (pixel value) at coordinates (x,y,z) of the three-dimensional data 300.

$$EnFace(x,y) = \int_{Dlow(x,y)}^{Dhigh(x,y)} Img(x,y,z) dz$$

Next, in Step S608, the display unit 440 displays the en-face image 310 generated by the generation unit 411. After that, the image processing apparatus 400 ends the processing in Step S609.

In this manner, in the image processing apparatus 400, the en-face image 310 is generated based on the en-face image generation rule relating to the past en-face image to be compared at the time of follow-up observation and the information on the layer boundary in the current three-dimensional data 300. With this configuration, the current and past en-face images that are generated for the eye to be inspected 200 under a similar condition can be compared with each other more accurately.

As described above, the image processing apparatus 400 according to the first embodiment includes the detection unit 412 configured to acquire the information on the layer boundary in the tomographic structure of the current eye to be inspected 200. Further, the image processing apparatus 400 includes the determination unit 430 configured to determine the depth range relating to the en-face image 310 of the current eye to be inspected 200 based on the information indicating the depth range relating to the past en-face image of the eye to be inspected 200 and the information on the layer boundary of the current eye to be inspected 200. Further, the image processing apparatus 400 includes the generation unit 411 configured to generate the current en-face image 310 of the eye to be inspected 200 through use of the data within the depth range relating to the en-face image 310 of the current eye to be inspected 200 among pieces of the three-dimensional data 300 acquired for the current eye to be inspected 200.

Accordingly, through use of the image processing apparatus 400, it is possible to generate the current en-face image 310 that is generated under the condition similar to that of the past en-face image of the eye to be inspected 200. Thus, through use of the image processing apparatus 400, the current and past en-face images can be compared with each other accurately, and hence the accuracy of follow-up observation can be enhanced. In addition, the depth range relating to the current en-face image 310 is determined based on the information indicating the depth range relating to the past en-face image, and hence it is possible to efficiently specify the en-face generation range for the acquired current three-dimensional data 300.

As the information indicating the depth range relating to the past en-face image, for example, information on a predetermined layer boundary, a distance from a predetermined layer boundary, or a ratio between distances from predetermined two layer boundaries can be used.

Further, as the three-dimensional data 300 to be used for generation of the en-face image 310, for example, a value of the OCT interference signal acquired by the image pickup optical system 100, a luminance value in the tomographic image of the eye to be inspected 200, a polarization parameter, or motion contrast data may be used. The motion contrast data is data indicating movement of the subject to be inspected, which is obtained by calculating a difference between tomographic images at substantially the same position that are picked up at different times. Thus, a part exhibiting movement can be detected through use of the motion contrast data, and, for example, a blood vessel image of the subject to be inspected can be generated through use of the motion contrast data as a pixel value. In particular, an OCTA image that is a blood vessel image can be generated through use of three-dimensional motion contrast data for the generation of the en-face image.

The source from which the image processing unit 410 acquires the three-dimensional data 300 on the current eye to be inspected 200 is not limited to the image pickup optical system 100. The image processing unit 410 may also acquire the three-dimensional data 300 on the current eye to be inspected 200 from, for example, the external server via a WAN, or a hospital database or other such freely-selected storage device via a LAN. Similarly, the image processing unit 410 may also acquire the three-dimensional data 300 on the past eye to be inspected 200 from, for example, the external server via the WAN, or the hospital database or other such freely-selected storage device via the LAN.

In the first embodiment, the acquisition unit is configured to acquire the information on the layer boundary in the tomographic structure of the current eye to be inspected 200 through use of the detection unit 412 configured to detect the layer boundary in the tomographic structure of the current eye to be inspected 200 from the three-dimensional data 300 of the current eye to be inspected 200. However, the configuration of the acquisition unit is not limited thereto. The acquisition unit may also acquire the information on the layer boundary in the tomographic structure of the current eye to be inspected 200 from, for example, the external server via the WAN, or the hospital database or other such freely-selected storage device via the LAN.

The image processing apparatus 400 according to the first embodiment further includes the storage unit 420 configured to store the information indicating the depth range relating to the past en-face image, and the determination unit 430 acquires the information from the storage unit 420. However, the source from which the determination unit 430 acquires the en-face image generation rule of the past en-face image is not limited to the storage unit 420. The determination unit 430 may also acquire the en-face image generation rule of the past en-face image from, for example, the external server via the WAN, or the hospital database or other such freely-selected storage device via the LAN.

Further, the image processing apparatus 400 according to the first embodiment further includes the display unit 440 configured to display the en-face image generated by the generation unit 411. The display unit 440 may also display a plurality of en-face images that are generated at different times, and display, on the tomographic image of the current eye to be inspected 200, the boundary lines indicating the depth range relating to the current en-face image 310 while displaying the tomographic image.

Second Embodiment

In the first embodiment, the en-face image generation rule of the past three-dimensional data is stored in the storage unit 420 or the like. In contrast to this, a case where the en-face image generation rule of the past three-dimensional data is not stored in the storage unit 420 or the like conceivable. An OCT apparatus according to a second embodiment of the disclosure is configured to apply a default rule (initial setting) to efficiently generate the current en-face image 310 of the eye to be inspected 200 when the en-face image generation rule of the past three-dimensional data is not stored in the storage unit 420 or the like. Respective components of the OCT apparatus according to the second embodiment have configurations similar to those of the respective components of the OCT apparatus according to the first embodiment, and are thus denoted by like reference numerals and description thereof is omitted.

Figure 9:
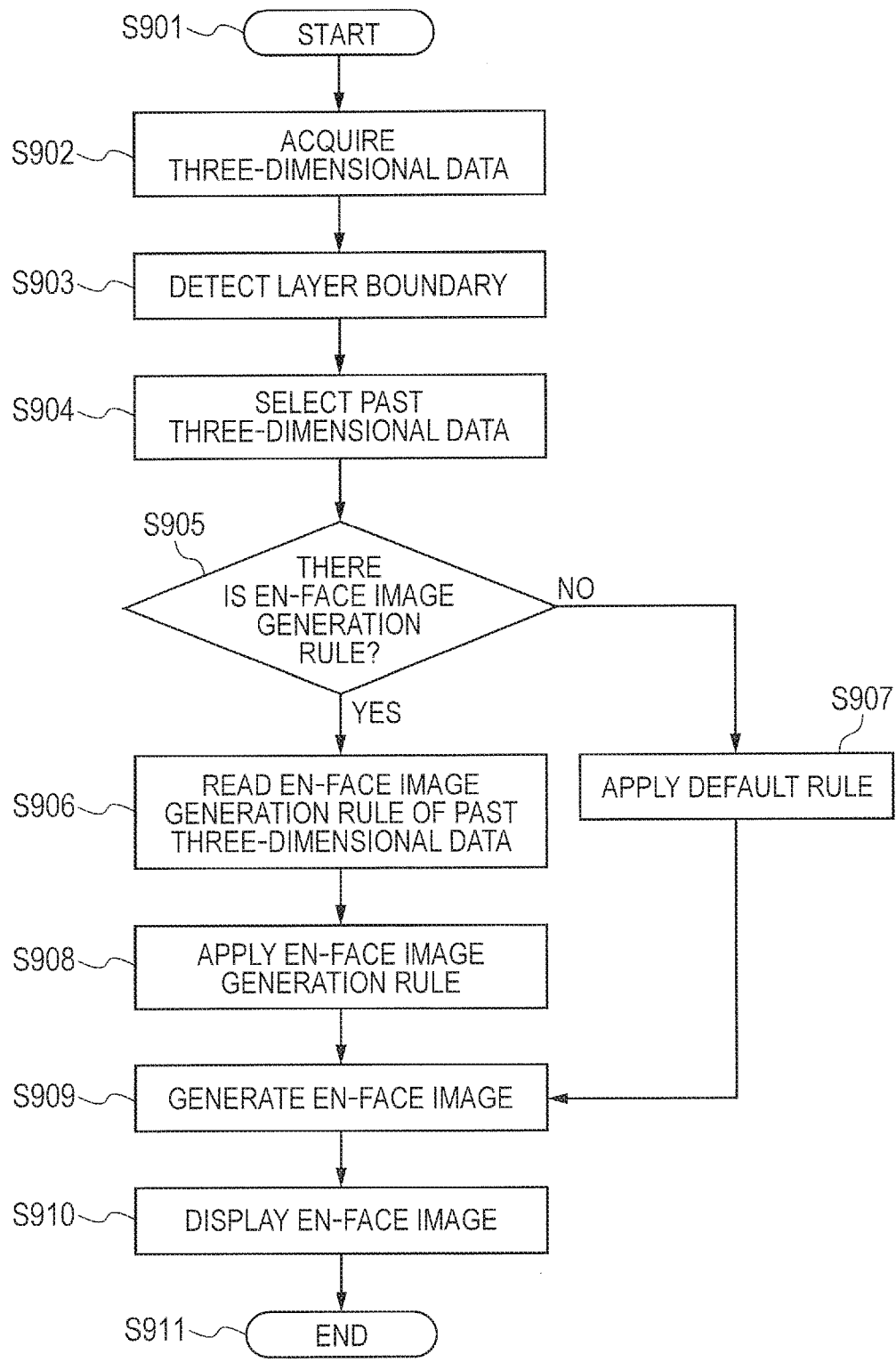
FIG. 9 is a flowchart for illustrating processing to be performed by an image processing apparatus according to a second embodiment.

Now, referring to FIG. 9, image processing of the second embodiment is described with a focus on differences from the image processing of the first embodiment. FIG. 9 is an illustration of a flow of the image processing in the image processing apparatus 400 according to the second embodiment, in which the case where the en-face image generation rule of the past three-dimensional data is not stored is taken into consideration.

In the image processing of the second embodiment, as in the image processing of the first embodiment, acquisition of the three-dimensional data (Step S902) and detection of the layer boundary (Step S903) are executed, and in Step S904, the past three-dimensional data is selected.

Next, in Step S905, the image processing unit 410 examines whether or not the en-face image generation rule is stored in the storage unit 420 (whether or not there an en-face image generation rule). When the en-face image generation rule is stored, the current en-face image 310 of the eye to be inspected 200 is generated and displayed by a flow similar to that of the image processing of the first embodiment (Step S906 to Step S910).

In contrast, when the en-face image generation rule is not stored in the storage unit 420, the image processing apparatus 400 shifts the processing to Step S907, in which a default en-face image generation rule (default rule) is applied. As a case where the en-face image generation rule is not stored, a case where the en-face image is not generated in the past three-dimensional data to be compared is conceivable.

In Step S907, the determination unit 430 applies a predetermined default en-face image generation rule that is set in advance to the current three-dimensional data 300 to determine the en-face generation range (depth range). Examples of the default en-face image generation rule include layer boundaries that are set in advance such as the NFL/GCL boundary and the GCL/TPL boundary. Further, as the default en-face image generation rule, a position specified in advance by the operator before use or the most frequently used rule among the en-face image generation rules that have been used for other patients may also be used.

After the en-face generation range is determined by the determination unit 430 based on the default en-face image generation rule, in Step S909, the generation unit 411 generates the en-face image 310. After that, in Step S910, the display unit 440 displays the en-face image 310 generated by the generation unit 411, and in Step S911, the image processing apparatus 400 ends the processing.

With the processing described above, even when the past en-face image generation rule is not stored in the storage unit 420 or the like, the image processing apparatus 400 can efficiently specify the generation range of the en-face image for the acquired current three-dimensional data 300. While the case where the past en-face image generation rule is not stored in the storage unit 420 is described in the above-mentioned example, similar processing is applicable even when the determination unit 430 acquires the past en-face image generation rule from a source other than the storage unit.

Further, a case where the past three-dimensional data to be compared is not stored in the storage unit 420 or the like in the first place is also conceivable. In such a case, the image processing apparatus 400 may determine in Step S904 that the past three-dimensional data is not stored, and shift the processing directly to Step S907 to apply the default rule to the current three-dimensional data 300.

As described above, in the image processing apparatus 400 according to the second embodiment, when the information indicating the depth range relating to the past en-face image not stored in the storage unit 420, the current en-face image 310 is generated in accordance with a predetermined rule. More specifically, when the information indicating the depth range relating to the past en-face image is not stored in the storage unit 420, the generation unit 411 generates the current en-face image 310 through use of data within a predetermined depth range among pieces of the three-dimensional data on the eye to be inspected 200. It is therefore possible to efficiently specify the generation range of the en-face image 310 for the acquired current three-dimensional data 300.

Third Embodiment

In the first and second embodiments, the en-face image generation rule or the default rule is applied to the current three-dimensional data 300 to generate the current en-face image 310. In contrast to this, after the screen for follow-up observation illustrated in FIG. 5 is displayed, the operator may desire to adjust the en-face generation range. In a third embodiment of the disclosure, in view of such a case, there is provided an OCT apparatus including an image processing apparatus 1000 capable of changing the en-face generation range (depth range) after the en-face image generation rule is applied.

Figure 10:
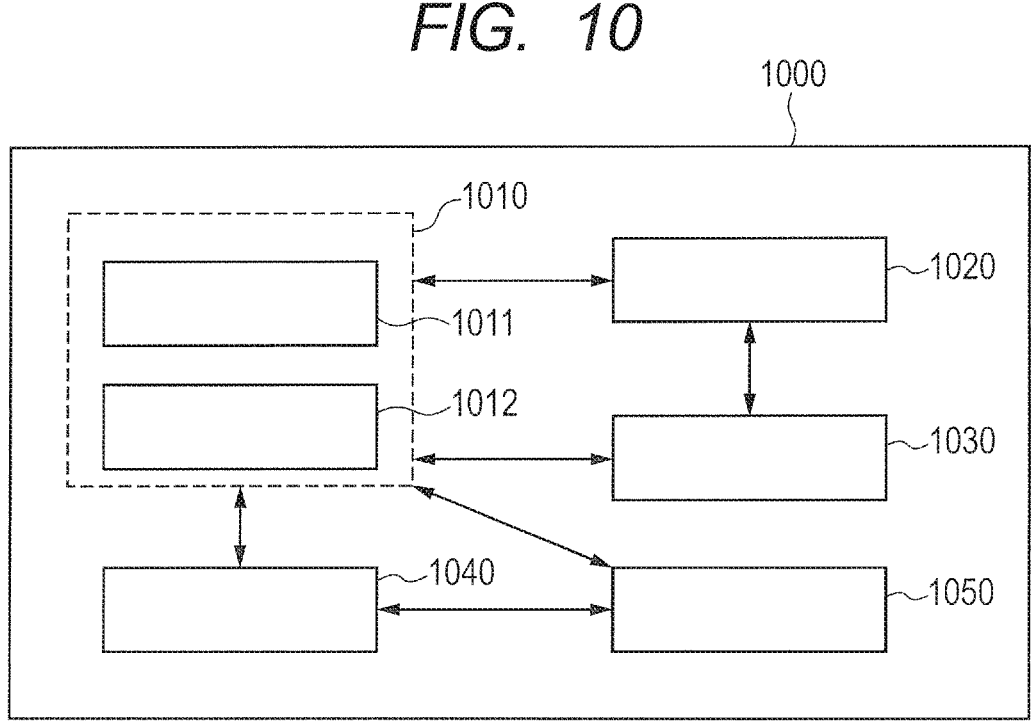
FIG. 10 is a block diagram for illustrating an example of a schematic configuration of an image processing apparatus according to a third embodiment.

Now, referring to FIG. 10, the image processing apparatus 1000 according to the third embodiment is described with a focus on differences from the image processing apparatus 400 according to the first embodiment. FIG. 10 is a block diagram for illustrating a schematic configuration of the image processing apparatus 1000 according to the third embodiment including a change unit 1050 configured to change the en-face generation range, that is, the en-face image generation rule. The image processing apparatus 1000 includes the change unit 1050 in addition to the components of the image processing apparatus 400 according to the first embodiment. The image processing unit 1010, the generation unit 1011, the detection unit 1012, the storage unit 1020, the determination unit 1030, and the display unit 1040 are similar to the respective components of the image processing apparatus 400 according to the first embodiment, and hence description thereof is omitted.

The change unit 1050 corresponds to the input unit 103 of FIG. 1. The change unit 1050 is capable of changing the en-face generation range determined by the determination unit 1030 in accordance with input from the input unit 103 such as the mouse and the keyboard. Specifically, the change unit 1050 can change the positions of the en-face generation range upper end 533 and the en-face generation range lower end 534 that are displayed in the layer display area 530 for the current three-dimensional data 300 of the display screen 500 illustrated in FIG. 5 in accordance with mouse dragging.

At this time, the generation unit 1011 generates the en-face image 541 in accordance with the change of the en-face generation range made by the change unit 1050, and the generated en-face image 541 is displayed in the en-face display area 540. With this configuration, the operator can adjust the en-face generation range after the en-face image is automatically generated and displayed, and it is therefore possible to enhance usability.

In a case where the operator adjusts the en-face image 541 in accordance with the target of follow-up observation, when the en-face generation range is adjusted, only the current en-face image 541 can be changed in accordance with mouse dragging. In contrast to this, a case where the operator desires to compare the target of follow-up observation whose depth range is changed with an en-face image within a depth range different from the one recorded in the past three-dimensional data is also conceivable. In this case, in accordance with the change of the current en-face generation range, the en-face generation range upper end 573, the en-face generation range lower end 574, and the en-face image 581 of the past three-dimensional data can also be changed in association with the change. With this configuration, it is possible to enhance the efficiency of comparison at the time of follow-up observation. The depth range may also be changed by, instead of mouse dragging, specifying the layer boundary or inputting the distance or ratio of the en-face image generation rule.

As described above, the image processing apparatus 1000 according to the third embodiment further includes the change unit 1050 configured to change the depth range relating to the current en-face image of the eye to be inspected 200. With this configuration, through use of the image processing apparatus 1000, the generation range of the en-face image for the acquired three-dimensional data can be efficiently specified and in a manner that suits the operator's intention.

While the Michelson interferometer is used as an interferometer of the image pickup optical system 100 in the above-mentioned first to third embodiments, a Mach-Zehnder interferometer may also be used. Depending on the difference in light intensity between the measurement light and the reference light, the Mach-Zehnder interferometer may be used when the difference in light intensity is large, whereas the Michelson interferometer may be used when the difference in light intensity is relatively small. Further, the configuration of the image pickup optical system 100 is not limited to the configuration described above, and a part of the components included in the image pickup optical system 100 may be a configuration that is separate from the image pickup optical system 100. Further, while the SLO is used as a unit configured to pick up the fundus image in the above-mentioned first to third embodiments, the fundus image may be picked up through use of a fundus camera or other such freely-selected image pickup unit.

Further, while the spectral-domain OCT (SD-OCT) apparatus, which uses the SLD as the light source, is described as the OCT apparatus in the above-mentioned first to third embodiments, the configuration of the OCT apparatus according to the present invention is not limited thereto. For example, the present invention is also applicable to a swept-source OCT (SS-OCT) apparatus, which uses a wavelength-swept light source capable of sweeping a wavelength of emitted light, or other such freely-selected type of OCT apparatus.

Further, the image processing units 410 and 1010 and the determination units 430 and 1030 of the image processing apparatus 400 and 1000 according to the above-mentioned first to third embodiments may be implemented through use of a dedicated circuit, or may be implemented by a CPU or other such arithmetic device.

According to the disclosure, it is possible to generate the en-face image for efficiently performing the follow-up observation of the subject to be inspected.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-133661, filed Jul. 5, 2016, which is hereby incorporated by reference herein in its entirety.

What is claimed is:

1. An image processing apparatus, comprising:
an acquisition unit configured to acquire information on a layer boundary in tomographic structure of a current subject to be inspected;
a determination unit configured to determine a depth range relating to a current en-face image of the subject to be inspected based on information indicating a depth range relating to a past en-face image of the subject to be inspected and the information on the layer boundary; and a generation unit configured to generate the current en-face image through use of data within the depth range relating to the current en-face image among pieces of three-dimensional data acquired for the current subject to be inspected.

2. An image processing apparatus according to claim 1, wherein the image processing apparatus is configured to use information on a predetermined layer boundary as the information indicating the depth range relating to the past en-face image.

3. An image processing apparatus according to claim 1, wherein the image processing apparatus is configured to use a distance from a predetermined layer boundary as the information indicating the depth range relating to the past en-face image.

4. An image processing apparatus according to claim 1, wherein the image processing apparatus is configured to use a ratio between distances from predetermined two layer boundaries as the information indicating the depth range relating to the past en-face image.

5. An image processing apparatus according to claim 1, further comprising a detection unit configured to detect, from the pieces of three-dimensional data, the layer boundary in the tomographic structure of the current subject to be inspected,
wherein the acquisition unit is configured to acquire the information on the layer boundary from the detection unit.

6. An image processing apparatus according to claim 1, further comprising a storage unit configured to store the information indicating the depth range relating to the past en-face image.

7. An image processing apparatus according to claim 6, wherein, when the information indicating the depth range relating to the past en-face image is not stored in the storage unit, the generation unit generates the current en-face image through use of data within a predetermined depth range in the subject to be inspected among the pieces of three-dimensional data.

8. An image processing apparatus according to claim 1, further comprising a display unit configured to display the current en-face image generated by the generation unit.

9. An image processing apparatus according to claim 8, wherein the display unit is configured to display a plurality of en-face images generated at different times.

10. An image processing apparatus according to claim 8, wherein the display unit is configured to display a tomographic image of the current subject to be inspected and to display, on the tomographic image, a boundary line indicating the depth range relating to the current en-face image.

11. An image processing apparatus according to claim 1, further comprising a change unit configured to change the depth range relating to the current en-face image.

12. An image processing apparatus according to claim 1, wherein the subject to be inspected comprises a fundus of an eye.

13. An image processing apparatus according to claim 1, wherein the en-face image comprises a blood vessel image.

14. An image pickup apparatus, comprising:
an image pickup unit configured to image a subject to be inspected to acquire three-dimensional data including layer information on the subject to be inspected;
a storage unit configured to store information indicating a depth range relating to a past en-face image of the subject to be inspected;
a detection unit configured to detect, from pieces of three-dimensional data on a current subject to be inspected, a layer boundary in tomographic structure of the current subject to be inspected;
a determination unit configured to determine, based on the information indicating the depth range relating to the past en-face image and the layer boundary, a depth range relating to a current en-face image of the subject to be inspected; and
a generation unit configured to generate the current en-face image of the determined depth range in three-dimensional data of the current subject to be inspected.

15. An image processing method, comprising:
acquiring information on a layer boundary in tomographic structure of a current subject to be inspected;
determining a depth range relating to a current en-face image of the subject to be inspected based on information indicating a depth range relating to a past en-face image of the subject to be inspected and the information on the layer boundary; and
generating the current en-face image of the depth range in three-dimensional data of the current subject to be inspected.

16. An image processing apparatus, comprising:
an acquisition unit configured to acquire information on a layer boundary in tomographic structure of a current subject to be inspected;
a determination unit configured to determine a depth range relating to a current en-face image of the subject to be inspected based on information indicating a depth range relating to a past en-face image of the subject to be inspected and the information on the layer boundary; and
a generation unit configured to generate the current en-face image of the determined depth range in three-dimensional data of the current subject to be inspected.

17. An image processing apparatus according to claim 16, further comprising a display unit configured to display the current en-face image generated by the generation unit,
wherein the display unit is configured to display a plurality of en-face images generated at different times.

18. An image processing apparatus according to claim 17, further comprising a change unit configured to change the depth range relating to the current en-face image,
wherein the display unit is configured to display a tomographic image of the current subject to be inspected and to display, on the tomographic image, a boundary line indicating the depth range relating to the current en-face image.

19. An image processing apparatus according to claim 16, wherein the subject to be inspected comprises a fundus of an eye.

20. An image processing apparatus according to claim 16, wherein the en-face image comprises a blood vessel image.

21. An image processing apparatus according to claim 16, wherein the en-face image is generated using a three-dimensional motion contrast data of the current subject to be inspected.

22. An image processing apparatus, comprising:
an acquisition unit configured to acquire information on a layer boundary in tomographic structure of a subject to be inspected using current three-dimensional data of the subject to be inspected;
a determination unit configured to determine, using information indicating a default depth range relating to an en-face image of the subject to be inspected and the information on the layer boundary, a part of data of the current three-dimensional data, the part of data corresponding to the default depth range;

a generation unit configured to generate a current en-face image of the subject to be inspected using the determined part of data; and a display control unit configured to display a past en-face image of the subject to be inspected and the current en-face image side by side on a display unit.

23. An image processing apparatus according to claim 22, wherein the information indicating the default depth range includes information indicating a depth range set initially.

24. An image processing apparatus according to claim 22, wherein the part of data includes a part of data of a current three-dimensional motion contrast data of the subject to be inspected, and wherein the past en-face image and the current en-face image includes a past motion contrast en-face image of the subject to be inspected and a current motion contrast en-face image of the subject to be inspected, respectively.

25. An image processing apparatus according to claim 22, wherein the display control unit is configured to display information indicating respective depth ranges relating to the past en-face image and the current en-face image on the display unit.

26. An image processing apparatus according to claim 22, further comprising a change unit configured to change a depth range relating to the current en-face image in response to an instruction from an operator, wherein the determination unit is configured to determine a part of data corresponding to the changed depth range.

27. An image processing apparatus according to claim 22, wherein the generation unit is configured to generate the current en-face image so that a depth range relating to the past en-face image and a depth range relating to the current en-face image correspond to each other.

28. An image processing method, comprising:

acquiring information on a layer boundary in tomographic structure of a subject to be inspected using current three-dimensional data of the subject to be inspected;

determining, using information indicating a default depth range relating to an en-face image of the subject to be inspected and the information on the layer boundary, a part of data of the current three-dimensional data, the part of data corresponding to the default depth ranges;

generating a current en-face image of the subject to be inspected using the determined part of data; and displaying a past en-face image of the subject to be inspected and the current en-face image side by side on a display unit.

29. A non-transitory computer-readable storage medium storing a program for causing a computer to execute the method according to claim 28.

30. A non-transitory computer-readable storage medium storing a program for causing a computer to execute the method according to claim 15.

* * * * *